United States Patent [19]

Suzuki et al.

[11] Patent Number: 4,787,070

[45] Date of Patent: Nov. 22, 1988

[54] COUPLER FOR ULTRASONIC TRANSDUCER PROBE

[75] Inventors: Akifumi Suzuki; Hiroshi Sasaki, both of Otawara, Japan

[73] Assignee: Kabushiki Kaisha Toshiba, Kanagawa, Japan

[21] Appl. No.: 67,124

[22] Filed: Jun. 29, 1987

[30] Foreign Application Priority Data

Jul. 29, 1986 [JP] Japan .................. 61-179187

[51] Int. Cl.4 ............................. H04R 23/00
[52] U.S. Cl. .................. 367/140; 181/400; 128/24 A; 128/660.1
[58] Field of Search ............ 73/642, 644; 310/335; 128/24 R, 660, 661, 662, 663; 367/140, 150; 181/400

[56] References Cited

U.S. PATENT DOCUMENTS

| 3,387,604 | 6/1968 | Erikson | 128/24 A |
|---|---|---|---|
| 3,934,460 | 1/1976 | Sherwin et al. | 73/642 |
| 3,982,223 | 4/1976 | Green | |
| 4,168,482 | 9/1979 | Sternberg | |
| 4,418,698 | 12/1983 | Dory | 128/660 |
| 4,435,985 | 3/1984 | Wickramasinghe | 73/642 |
| 4,503,861 | 3/1985 | Entrekin | 73/642 |
| 4,579,123 | 4/1986 | Chen et al. | 73/644 |
| 4,603,701 | 8/1986 | Chen | 73/644 |

FOREIGN PATENT DOCUMENTS 57-136304  8/1982  Japan .

Primary Examiner—Charles T. Jordan
Assistant Examiner—John W. Eldred
Attorney, Agent, or Firm—Finnegan, Henderson, Farrabow, Garrett, & Dunner

[57] ABSTRACT

A coupler for use between an ultrasonic transducer probe and a sample to be examined thereby to keep the ultrasonic transducer probe and the sample spaced a prescribed distance from each other includes an acoustic lens in an area through which a ultrasonic signal is to pass from the ultrasonic transducer probe. The acoustic lens allows the focusing point of the lens of the ultrasonic transducer probe to be shifted to a desired position. Since the ultrasonic transducer probe and the sample are spaced from each other by the coupler, the image of an observed region of the sample can be positioned in a wide field of view on a screen.

4 Claims, 4 Drawing Sheets

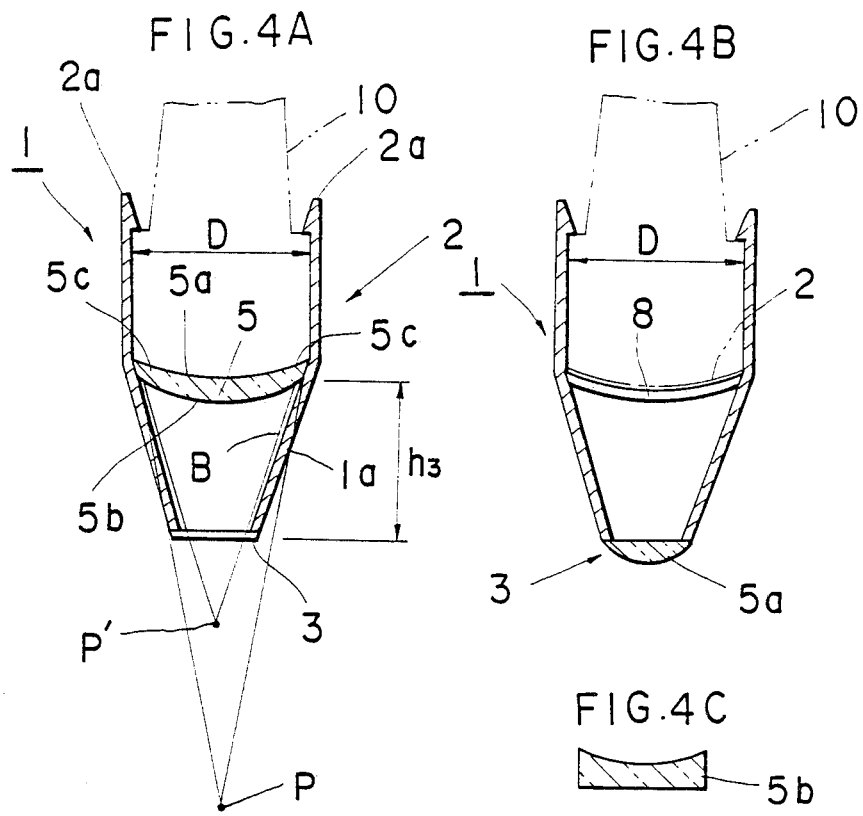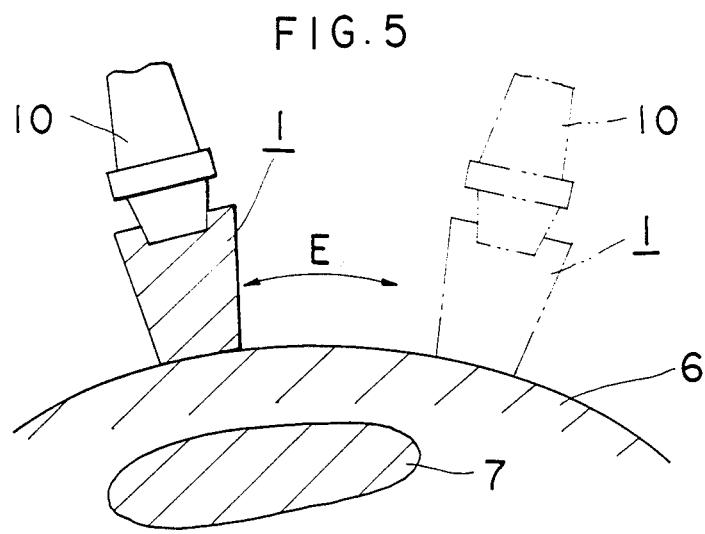

COUPLER FOR ULTRASONIC TRANSDUCER PROBE

BACKGROUND OF THE INVENTION

The present invention relates to a coupler for use with an ultrasonic transducer probe for transmitting ultrasonic waves to or receiving ultrasonic waves from a target region in a sample or object under examination.

Where a living human body is examined for medical diagnosis to observe a superficial organ such as a thyroid gland or a carotid artery with a sector-shaped beam emitted from a sector-type ultrasonic transducer probe, it is necessary to position the focusing point of a lens attached to the tip end of the probe in the vicinity of the observed region. To meet such a requirement, a coupler is mounted on the ultrasonic transducer probe for keeping the probe spaced a prescribed distance from the surface of the living body being examined. Such a coupler is illustrated in FIGS. 8 and 9 of the accompanying drawings. FIG. 8 is a sectional front elevational view of the copuler, the plane as viewed in FIG. 8 being referred to as a scanning plane. FIG. 9 is a sectional side elevational view of the coupler, the plane as viewed in FIG. 9 being referred to as a plane normal to the scanning plane. A coupler C is mounted on the tip end of a sector-scanning ultrasonic transducer probe 11. The coupler C has a mounting surface 2 which is mounted on the probe 11 and an abutting surface 3 which will be held against an object to be examined. The coupler C is in the shape of a rectangular parallelepiped as a whole and has a height h, a length L in the scanning plane, and a width W in the plane normal to the scanning plane.

When the coupler C is employed, the focusing point P of the lens of the probe 11 is closer to the observed region by the height h than focusing point P is when such coupler C is not employed.

Where the target region to be observed is positioned not deeply below the surface of the object living body, it is necessary to use a coupler of a larger height h in order to bring the focusing point P into conformity with the observed region. This causes the following problems:

The first problem is that as the coupler height h is increased, the length L and the width W of the coupler are also increased, resulting in a large coupler size which cannot be handled with ease.

The second problem will be described with reference to FIG. 10, which shows the relationship bewteen gains of the probe and coupler heights according to a STC (Sensitivity Time Control) curve for a signal received by the probe. In case a human body is diagnosed by an ultrasonic transducer probe, a signal received from an observed region by the probe is generally weaker as the region is located more deeply in the body, i.e., as the depth of the region is greater. Such a signal level variation is compensated for by employing the STC curve to correct the received signal. The interior of the coupler is usually filled with water in which ultrasonic energy is substantially not attenuated. Where couplers C1, C2 having different heights h1, h2, respectively, are employed, no problem is caused by the coupler C1 of the smaller height h1 as its gain G1 is small, but the larger gain G2 of the coupler C2 of the larger height h2 amplifies multiple reflection in a member positioned on the surface of the coupler C which contacts the living body under examination. Such amplified multiple reflection results in an artifact on the reproduced image, presenting an obstacle to the proper reading of the image. Therefore, the coupler for use with an ultrasonic transducer probe should not be of a large height.

Japanese Utility Model Laid-Open Publication No. 57-136304 discloses, as shown in FIG. 11 of the accompanying drawings, a linear-scanning ultrasonic transducer probe 11' having an ultrasonic wave transmission/reception surface 15 and combined with a converter 12 with an acoustic lens 16 held against the ultrasonic wave transmission/reception surface 15. The disclosed arrangement is however capable of only shifting the focusing point for transmitted and received ultrasonic waves, but is not based on any idea of keeping the probe and an examined object spaced a prescribed distance from each other.

SUMMARY OF THE INVENTION

In view of the aforesaid drawbacks of the conventional couplers, it is an object of the present invention to provide a coupler for use with an ultrasonic transducer probe, capable of bringing the focusing point of a lens of the probe into exact agreement with a region being observed by the probe.

Another object of the present invention is to provide a coupler for use with an ultrasonic transducer probe, which can be handled well.

Still another object of the present invention is to provide a coupler for use with an ultrasonic transducer probe, which can produce images in a large field of view.

To achieve the above objects, a coupler is adapted to be mounted on an ultrasonic transducer probe for us between the probe and a sample or object under examination to keep them spaced a prescribed distance from each other, the coupler having an acoustic lens in an area through which an ultrasonic signal from the probe passes. Since the acoustic lens is employed in the coupler, the focusing point of a lens of the probe can be shifted to a desired position. Inasmuch as ultrasonic transducer probe and the examined object are spaced the prescribed distance from each other, an observed region can be positioned in a wide field of view on a screen.

The above and other objects, features and advantages of the present invention will become more apparent from the following description when taken in conjunction with the accompanying drawings in which preferred embodiments of the present invention are shown by way of illustrative example.

BRIEF DESCRIPTION OF THE DRAWINGS

FIG. 4A is a cross-sectional view of the coupler of FIG. 1;

FIG. 4B is a cross-sectional view of a coupler according to another embodiment of the present invention;

FIG. 4C is a cross-sectional view of another acoustic lens that can be used in the coupler illustrated in FIG. 4B;

FIG. 5 is a cross-sectional view showing the manner in which the coupler of the invention is used;

DESCRIPTION OF THE PREFERRED EMBODIMENTS

Figure 1:
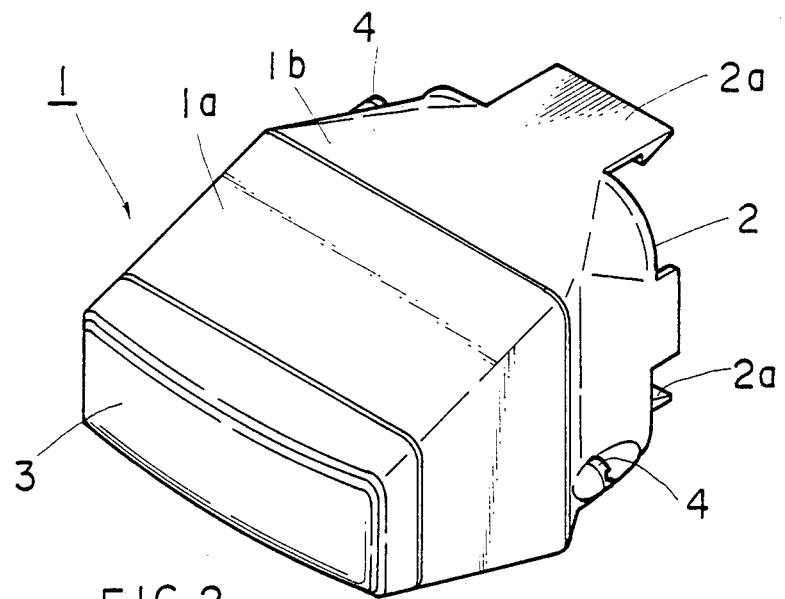
FIG. 1 is a perspective view of a coupler for an ultrasonic transducer probe according to the present invention.
Figure 2:
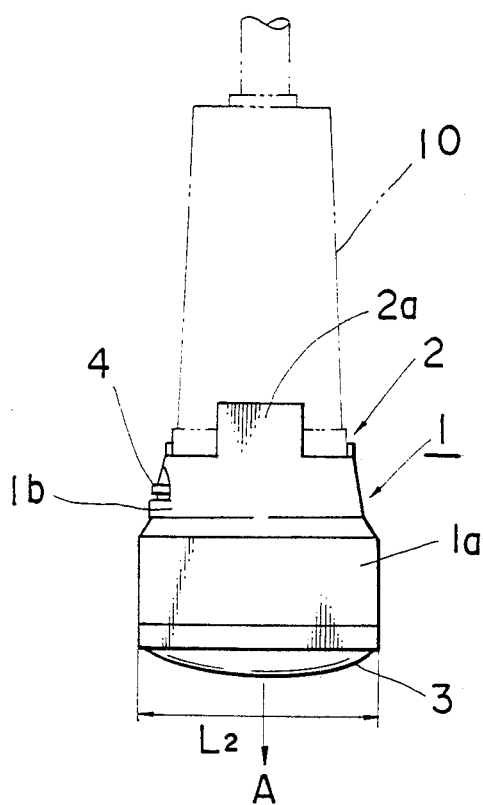
FIG. 2 is a front elevational view of the coupler shown in FIG. 1.
Figure 3:
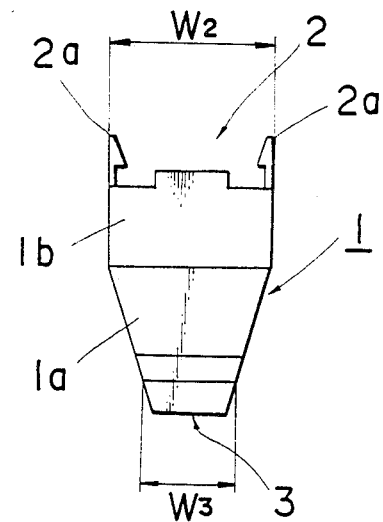
FIG. 3 is a side elevational view of the coupler of FIG. 1.

A coupler for use with an ultrasonic transducer probe according to the present invention will first be described with reference to FIGS. 1 through 3.

The coupler, generally designated by the reference numeral 1, comprises a main body 1a of a hollow structure having a trapezoid cross section and a mounting member 1b for attachment to the ultrasonic transducer probe. The mounting member 1b has an upper surface serving as a mounting surface 2. The main body 1a has a bottom surface serving as a contact surface 3 for contact with a sample or object such as a human body to be examined. The mounting member 1b has a pair of spaced side walls 2a with inwardly projecting hooks on their upper ends, respectively. As shown in FIG. 2, the ultrasonic transducer probe, denoted at 10, has its distal end fitted between and locked by the side walls 2a.

In a plane (focusing plane) normal to the direction of the arrow A (FIG. 2) in which an ultrasonic beam is scanned, the contact surface 3 has a width W3 which is smaller than the width 1b of the mounting member W2.

As shown in FIG. 4A, an acoustic lens 5 is mounted at the mounting surface 2. The acoustic lens 5 has an upper surface 5a having a radius of curvature which is the same as that of an acoustic lens of the probe 10, and a lower surface 5b having a radius of curvature which is smaller than that of the upper surface 5a. Therefore, the acoustic lens 5 has a focusing point P' which is closer toward the probe 10 than the focusing point P of the lens of the probe 10. A suitable acoustic damper may be disposed at each of opposite ends 5c of the acoustic lens 5 to reduce the aperture D for thereby increasing the resolution of a received signal from a shallow region in the object. An acoustic coupling agent such as ultrasound gel may be disposed between the probe 10 and the acoustic lens 5 for allowing ultrasonic waves to be transmitted smoothly therebetween.

Figure 7:
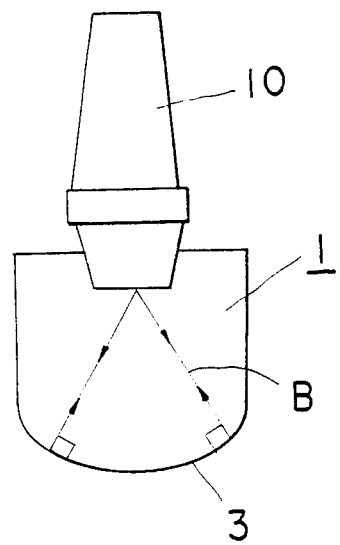
FIG. 7 is a side elevational view showing the manner in which the coupler of the invention is used in a different way.

The contact surface 3 of the coupler 1 has a convex curved shape having a certain radius of curvature. The radius of curvature of the contact surface 3 may be such that an ultrasonic beam B (FIG. 7) emitted from the probe 10 will be applied to the contact surface 3 at a right angle or a substantially right angle at any point thereon since the beam B thus applied can well be transmitted through the contact surface 3 and a reflected beam is reduced in diameter.

The coupler 1 may be constructed as either an outer shell of plastics containing therein an acoustic medium such as water or other solution, or a holder containing a solid colloidal body. Where the acoustic medium such as water or other solution is filled in the outer shell of the coupler 1, the contact surface 3 is composed of a membrane of silicone rubber. The acoustic medium is introduced into the coupler 1 through a inlet 4 (FIGS. 1 and 2).

Figure 10:
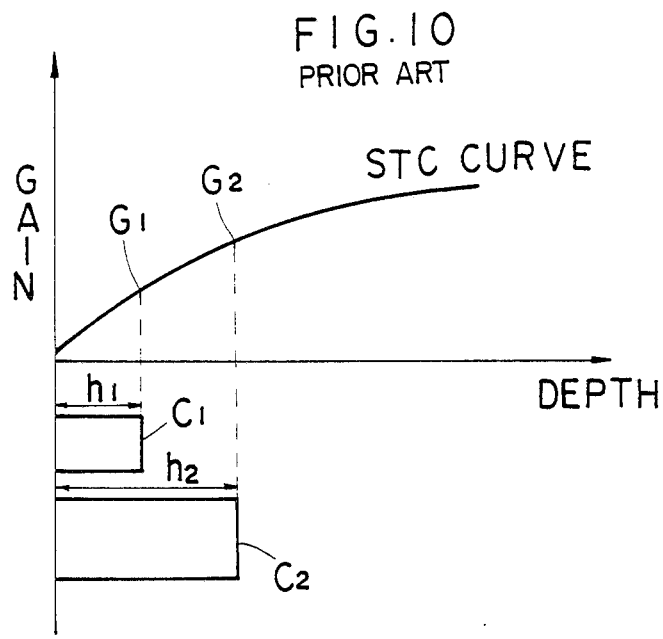
FIG. 10 is a graph illustrative of a problem of the conventional coupler.

The main body 1a of the coupler 1 has a height h3 (FIG. 4A) which is smaller than the heights h1, h2 of the conventional couplers C1, C2 (FIG. 10), and a length L2 (FIG. 3) which is also smaller than the length L1 (FIG. 8) of the conventional coupler C. This is because the coupler 1 of the invention may be smaller in overall size on account of the acoustic lens 5 though the coupler 1 remains functionally the same as the conventional couplers.

FIG. 4B shows a coupler according to another embodiment of the present invention. The coupler includes an acoustic lens 5a disposed at a contact side 3 for contact with an object to be examined. A membrane 8 of silicone rubber is disposed on a contact surface 2 which is to be held against the ultrasonic transducer probe 10. The acoustic lens 5a has an inner flat surface and an outer convex surface. Alternatively, an acoustic lens 5b that can be used in the coupler of FIG. 4B may have an inner concave surface and an outer flat surface, as shown in FIG. 4C.

Figure 6:
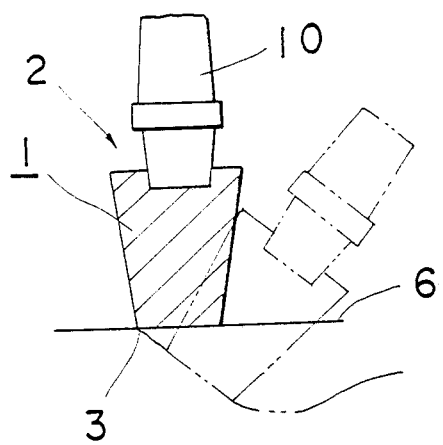
FIG. 6 is a view explaining the shape of a tip end of the coupler.

The coupler 1 is used in the following manner:

As shown in FIG. 5, a coupler 1 with its focusing point on an observed region 7 is selected and mounted on the ultrasonic transducer probe 10. Then, the coupler 1 is held in contact with an object 6 to be examined while ultrasonic waves are being transmitted from the probe 10 toward the object 6 and a reflected ultrasonic beam is being received by the probe 10. While the coupler 1 is thus operated, it is pressed against the surface of the object 6 as shown in FIG. 6, so that the observed region 7 can be viewed directly (pivot scanning).

The coupler 1 thus constructed and operated offers the following advantages:

(a) The acoustic lens 5 is disposed at the mounting surface 2 for attachment to the probe 10, and the radius of curvature of the upper surface 5a of the acoustic lens 5 is the same as that of the acoustic lens of the probe 10 whereas the radius of curvature of the lower surface 5b of the acoustic lens is smaller than that of the upper surface 5a, so that the focusing point P' of the acoustic lens 5 is shifted closer toward the probe 10 than the focusing point of the lens of the probe 10 itself. Therefore, the coupler 5 allows the image of a superficial organ such as a thyroid gland or a carotid artery to be observed with a high image quality at a high resolution and in a wide field of view. Since the coupler 1 does not need to be increased in size, it can be handled easily. As the height h2 of the coupler 1 is made small, any artifact caused by multiple reflection at the contact surface or window member 3 is so reduced that it will not obstruct diagnosis or image reading.

Since the focusing point P' is located in any desired position by the acoustic lens 5, the freedom in designing the shape of the coupler can be increased greatly.

(b) Inasmuch as the contact surface 3 for contacting the surface of an object 6 such as a human body under examination is of a convex curved shape having a prescribed radius of curvature, any multiple reflection at the sides of the coupler 1 can be reduced, and the coupler 1 can snugly be held against the surface of the object 6.

Figure 8:
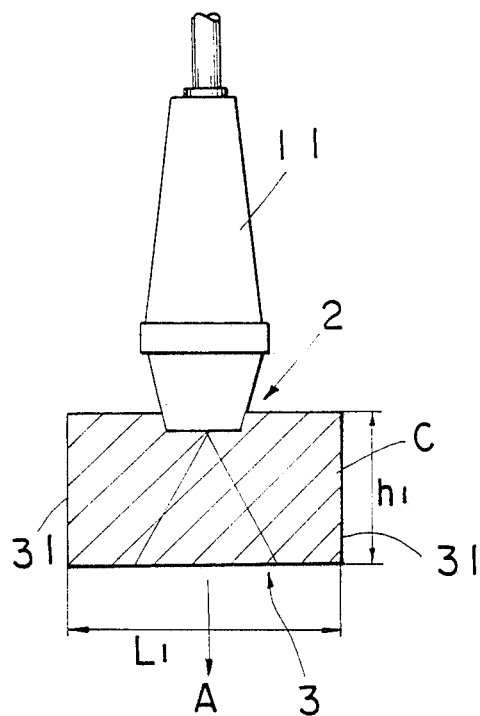
FIG. 8 is a sectional front elevational view of a conventional coupler.

The conventional couplers are in the form of a water bag or a pliable solid body such as a colloidal mass, having a flat or freely deformable contact surface for contact with a surface over a target region (i.e., a human body surface). Therefore, if the surface over the target region is flat, then the contact surface 3 is also made flat. Thus, as shown in FIG. 8, the bottom surface 3 and opposite side surfaces 31 of the coupler C cause reflections which are responsible for multiple-reflected images or artifacts on the monitor of an ultrasonic imaging apparatus, resulting in an obstacle to diagnosis or image reading.

With the present invention, however, the contact surface 3 of the coupler 1 is of a convex curved shape having a prescribed radius of curvature such that the transmittivity of the contact surface 3 with respect to ultrasonic beams is increased whereas reflected beams are weakened. Consequently, multiple reflections on the sides of the coupler 1 are reduced, and hence so are the influence of multiple-reflected images on the monitor of an ultrasonic imaging apparatus, with the result that diagnosis or image reading can smoothly be effected.

The convex curved contact surface 3 allows the coupler 1 to be snugly held in contact with the body surface 6.

(c) The width W3 of the contact surface 3 in a direction normal to the scanning direction A of the ultrasonic transducer probe 10 is smaller than the corresponding width of the contact surface of conventional couplers. This is advantageous in that when the contact surface 3 moves on the body surface 6 as shown in FIG. 5, it is subject to less friction and can be moved smoothly, and when the coupler 1 is angularly moved about a pivot on the body surface 6 as shown in FIG. 6, the contact surface 3 can easily be pressed into the body surface 6 and well be held against the body surface 6.

Figure 9:
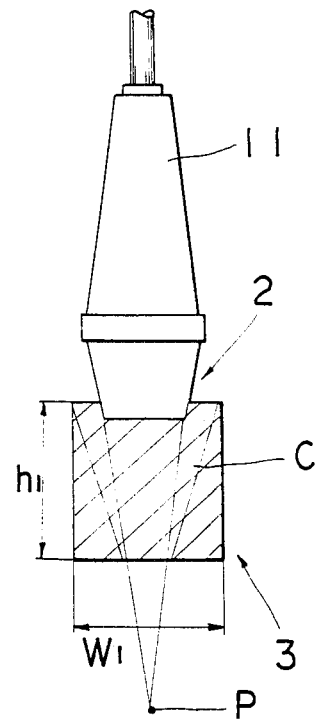
FIG. 9 is a sectional side elevational view of the coupler of FIG. 8.

With the conventional coupler, however, as shown in FIGS. 8 and 9, both cross-sectional shapes thereof in the scanning direction A and the direction normal thereto are rectangular, and hence the width W1 of the contact surface is relatively large. When the coupler is moved on the body surface, it undergoes large friction and cannot be moved smoothly. At the time of angularly moving the coupler about a pivot on the body surface, it cannot sufficiently be pressed into the body surface and hence its contact with the body surface is poor.

It can easily be understood that the coupler of the present invention can solve the aforesaid problems of the conventional couplers.

Figure 11:
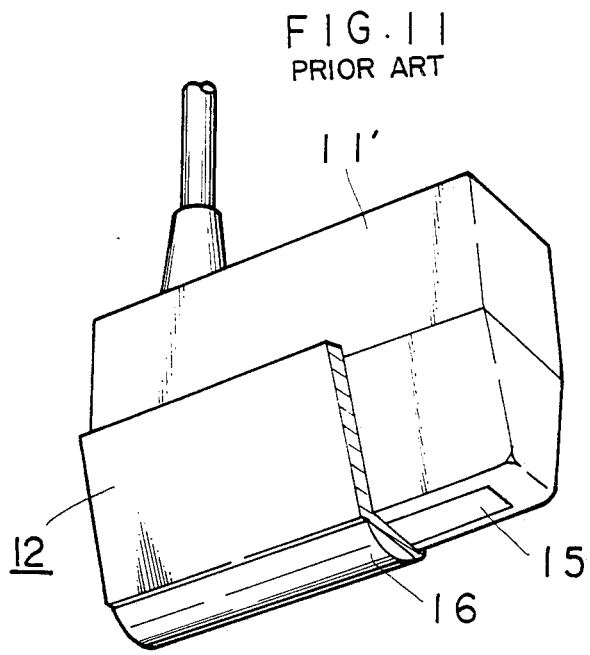
FIG. 11 is a perspective view, partly cut away, of a known coupler.

The present invention is applicable to not only a coupler for use with a sector-scanning ultrasonic transducer probe, but also a coupler for use with a linear-scanning ultrasonic trandducer probe 11' as shown in FIG. 11.

Although certain preferred embodiments have been shown and described, it should be understood that many changes and modifications may be made therein without departing from the scope of the appended claims.

What is claimed is:

1. A coupler for use between an ultrasonic transducer probe and a sample to be examined thereby to keep the untrasonic transducer probe and the sample spaced a prescribed distance from each other, said coupler comprising:
   a hollow main body having distal and proximal ends, a trapezoidal cross section, and a contact surface disposed on the distal end adapted for contact with the sample to be examined;
   a mounting member, disposed on the proximal end, for attachment to an ultrasonic transducer probe;
   said main body having, between said mounting member and said contact surface, a larger width in a scanning direction in which a beam from the ultrasonic transducer probe is scanned and a smaller width in a focusing direction normal to said scanning direction; and
   an acoustic lens disposed on the coupler.

2. A coupler according to claim 1, wherein said mounting member includes a mounting surface, said acoustic lens being disposed on said mounting surface.

3. A coupler according to claim 2, wherein said acoustic lens has a first surface, held against said mounting surface, having a first radius of curvature; and
   a second surface, opposite to said first surface, having a second radius of curvature smaller than said first radius of curvature.

4. A coupler according to claim 1, wherein said acoustic lens is disposed on said contact surface.

* * * * *